United States Patent [19]

Sawai et al.

[11] Patent Number: 5,089,265
[45] Date of Patent: Feb. 18, 1992

[54] STABILIZED PHYTIC ACID COMPOSITIONS

[75] Inventors: Kiichi Sawai, Funabashi; Masayasu Kurono, Mie; Hiromoto Asai, Nagoya; Takahiko Mitani, Mie; Naohisa Ninomiya, Nagoya, all of Japan

[73] Assignee: Sanwa Kagaku Kenkyusho Co., Ltd., Nagoya, Japan

[21] Appl. No.: 427,228

[22] Filed: Oct. 24, 1989

[30] Foreign Application Priority Data

Nov. 1, 1988 [JP] Japan .................. 63-276386

[51] Int. Cl.$^5$ .................. A61K 35/00; A61K 35/78; C12P 01/00
[52] U.S. Cl. .................. 424/195.1; 514/57; 514/60
[58] Field of Search ............ 424/195.1, 52; 426/618; 514/55, 57, 60

[56] References Cited

U.S. PATENT DOCUMENTS

| | | | |
|---|---|---|---|
| 3,846,397 | 11/1974 | Ernster | 260/112 R |
| 4,259,316 | 3/1981 | Narashima | 424/52 |
| 4,305,928 | 12/1981 | Harvey | 424/52 |
| 4,335,102 | 6/1982 | Nakashima | 424/52 |
| 4,758,430 | 7/1988 | Sabin | 424/94.1 |
| 4,826,675 | 5/1989 | Gaffar | 424/52 |
| 4,929,774 | 5/1990 | Fukamachi | 568/824 |

*Primary Examiner*—Ronald W. Griffin
*Assistant Examiner*—Ralph Gitomer
*Attorney, Agent, or Firm*—Armstrong, Nikaido, Marmelstein, Kubovcik & Murray

[57] ABSTRACT

A stabilized phytic acid composition is provided, which comprises phytic acid or its salt and at least one stabilizer selected from the group consisting of a product obtained by the lactic fermentation and ripening of rice bran, a water-soluble polymer capable of forming a film and an additive capable of absorbing water.

1 Claim, No Drawings

STABILIZED PHYTIC ACID COMPOSITIONS

BACKGROUND OF THE INVENTION

1. Field of the Invention

The present invention relates to a composition containing phytic acid or a salt thereof which is stabilized and enhanced in its pharmacological activity.

2. Prior Art

Phytic acid is unstable liquid substance which may be powdered or otherwise treated by methods disclosed in Japanese Patent Publication No. SHO 63-32074(B2), published June 28, 1988, and corresponding to Japanese Patent Application No. SHO 55-174126, filed Dec. 9, 1980.

The inventors have already found that phytic acid is effective for deodorization due to its actions upon the prevention of in vivo decomposition and generation of ill-smelling substances, detoxification due to the decomposition of harmful substances in excitometabolic systems, and so on. During the investigation of such actions, the present inventors have now discovered that the action of phytic acid varies from preparatory lot to preparatory lot because it decomposes and polymerizes.

Phytic acid produces a strong action in relatively small amounts, when administrated in pure form, but is likely to change chemically. Phytic acid is also desired to be stably absorbed, when administered to a living body. The situation being now like this, a large amount of phytic acid is administered in consideration of its decomposition, thus offering side-effect problems such as gastrointestinal tract disorders, mineral deficiencies and electrolyte dysbolism.

The inventors have now discovered that when orally administered in the process of nutrition experiments, phytic acid is effective in the removal of body smells, esp., bad breath, urinary smell and sweaty smell. Particularly, detailed studies of workings of the removal of the smell of garlic have revealed that this is attributable to the antienzymatic action or in vivo excitometabolic action of phytic acid. Further, the inventors have found that phytic acid is effective for the reduction of glucosuria and lipid, the promotion of erythrodegenerative power, defense under low oxygen loads and the recovery of the retentive faculty. Still further, the inventors have noted that phytic acid is effective for the inhibition of progression, prevention and treatment of hectic diseases by functional regression, esp., geriatric diseases. Consequently, the inventors have found a biochemically and physicochemically stable pharmaceutic composition which can make effective use of such actions without causing side-effects.

SUMMARY OF THE INVENTION

The present invention has for its object to provide a composition comprising phytic acid or its salt and at least one biochemically and physicochemically stable stabilizer selected from the group consisting of a product obtained by the lactic fermentation and ripening of rice bran, lactose and crystalline cellulose, which is easily administrable by an oral route and is expected to prevent the side-effects of phytic acid and achieve biochemical and physicochemical stability in the oral administration of phytic acid or its salt admixed with food and drink, sprinkled over dishes or in a powdery or granular state.

More specifically, according to one aspect of the present invention, there is provided a stabilized phytic acid composition comprising phytic acid or its salt and at least one stabilizer selected from the group consisting of a product obtained by the lactic fermentation and ripening of rice bran, a water-soluble polymer capable of forming a film and an additive capable of absorbing water.

DETAILED DESCRIPTION OF THE INVENTION

It is understood that the phytates usable in the present invention may include potassium phytate, sodium phytate, ammonium phytate, arginine phytate, ornithine phytate, lysine phytate, histidine phytate, monoethanolamine phytate, diethanolamine phytate, triethanolamine phytate and glucamine phytate, by way of example.

The number of moles of various bases required to regulate one mole of phytic acid to pH 6 to 8 is shown in Table 1.

TABLE 1

| Bases/pH | 6.00 | 7.00 | 8.00 |
|---|---|---|---|
| NaOH | 7.34 | 8.21 | 8.94 |
| KOH | 7.34 | 8.23 | 8.94 |
| LiOH | 7.41 | 8.38 | 9.30 |
| $NH_4OH$ | 7.61 | 8.55 | 9.45 |
| $HOC_2HCH_2NH_2$ | 7.72 | 8.68 | 9.52 |
| $(HOCH_2CH_2)_2NH$ | 7.54 | 8.45 | 9.31 |
| $(HOCH_2CH_2)_3N$ | 7.20 | 8.53 | 12.1 |
| N-Methylglucamine | 7.62 | 8.49 | 9.25 |
| L-Arginine | 7.79 | 8.67 | 9.60 |
| L-Lysine | 8.01 | 8.98 | 10.0 |
| L-Histidine | 11.3 | — | — |

Examples of the water-soluble polymers capable of forming a film, which can be used as the stabilizers in the present invention, may include:

(1) Natural water-soluble polymers
Decomposed products of starch (dextrin)
α-starch
Starch derivatives (starch esters or ether or crosslinked starch)
Pullulan
Cellulose sodium glycolate
Methyl cellulose
Hydroxyethyl cellulose
Hydroxypropyl cellulose
Hydroxymethylpropyl cellulose
Arginic acid
Guar gum
Tragacanth gum
Tamarindus indica (Leguminosae) seed polysacchrides
Gelatin (2) Synthetic water-soluble polymers
Sodium polyacrylate
Polyacrylamide
Polyvinyl alcohol
Polyvinyl pyrrolidone
Polyethylene oxide
Crosslinked type acrylic polymer Examples of the water-absorptive additive materials may include:

(1) Saccharides
Lactose
Saccharose
Dextrose
Mannitol
Sorbitol (2) Inorganic materials
Calcium hydrogen phosphate Calcium nitrate
Light silicic anhydride
(3) Celluloses
Crystalline cellulose
α-cellulose
Carboxymethyl cellulose
Carboxymethyl cellulose calcium
Hydroxypropyl cellulose having a low degree of substitution
(4) Starches
Corn starch
Potato starch
Rice starch
Partial α-starch
Carboxymethyl starch sodium
Hydroxypropyl starch
(5) Chitosan It is noted that added to and mixed with phytic acid or its salt are the product obtained by the lactic fermentation and ripening of rice bran, lactose and/or crystalline cellulose in an amount of 0.5 to 30% by weight.

Effect of the Invention

In short, the composition containing phytic acid or its salt as the main component and including at least one stabilizer selected from the group consisting of the product obtained by the lactic fermentation and ripening of rice bran, lactose, crystalline cellulose and the like according to the present invention makes effective use of the actions of phytic acid. According to this invention, that composition is orally administrable in an easier manner than is achievable with phytic acid or its salt alone.

Further, the composition of this invention is very stable and continuously administrable, and can extract the effective pharmacological actions of phytic acid by continued use or administration.

EXAMPLE OF FORMULATIONS

Mixture Containing the Product Obtained by the Lactic Fermentation and Ripening of Rice Bran

| Prescription | |
|---|---|
| Phytic acid | 100 g |
| Product obtained by the lactic fermentation and ripening of rice bran | Suitable Amount |
| Total: | 1000 ml |

EXAMPLES OF PREPARATIONS

Preparation Example 1: Composition Obtained by the Lactic Fermentation and Ripening of Rice Bran

| Prescription | |
|---|---|
| Mixture obtained by the lactic fermentation and ripening of rice bran | 600 ml |
| Dextrin | 473 g |
| Esculent pigment Yellow No. 4 | 25 mg |
| Esculent pigment Yellow No. 5 | 25 mg |
| Refined water | 180 ml |
| Total: | 500 g calculated as solid |

A liquid obtained by the dissolution of the components according to the above prescription is powdered at an air feed temperature of 155° C. and an air discharge temperature of 55° C. with the use of a spray dryer.

Preparation Example 2: Liquid Phytate Composition

| Prescription | |
|---|---|
| Phytic acid (50%) | 365.3 g |
| Alkaline solution (potassium hydroxide: 3.675 N and sodium hydroxide: 1.25 N) | 1284 ml |
| Calcium chloride.2H$_2$O | 3.368 g |
| Disodium hydrogen phosphate.12H$_2$O | 139.5 g |
| Refined water | Suitable Amount |
| Total: | 2000 ml |

According to the above prescription, the components are dissolved into a liquid phytate composition.

Preparation Example 3: Containing Lactose

| Prescription | |
|---|---|
| Liquid phytate composition | 14.4 ml |
| Lactose | Suitable Amount |
| Powdery gum arabic | 2.00 g |
| Total: | 100 g calculated as solid |

According to the above prescription, the components are weighed and kneaded together. The kneaded product is granulated with a basket of 0.8 mmφ, followed by particle size regulation with a 16-mesh sieve. Thereafter, the granular product is dried at 60° C. for 1 hour into granules.

Preparation Example 4: Containing Crystalline Cellulose

| Prescription | |
|---|---|
| Liquid phytate composition | 14.4 ml |
| Crystalline cellulose lactose | Suitable Amount |
| Powdery gum arabic | 2.00 g |
| Total: | 100 g calculated as solid |

According to the above prescription, the components are weighed, mixed together, stirred and granulated. The granulated product is then regulated to a suitable granular size through a 32-mesh sieve. Thereafter, the granular product is dried at 60° C. for 1 hour into fine granules.

Preparation Example 5: Containing Partial α-Starch

| Liquid phytate composition | 1095 ml |
|---|---|
| Crystalline cellulose | 518.0 g |
| Corn starch | 518.0 g |
| Lactose | Suitable Amount |
| Partial α-starch | 414.0 g |
| Aspartame | 18.00 g |
| Sucrose fatty acid ester | 15.00 g |
| Total: | 3000 g calculated as solid |

According to the above prescription, the components except the sucrose fatty acid ester are kneaded together with the addition of a suitable amount of refined water. The thus kneaded product is granulated with a basket of 1.00 mmφ, and is then regulated to a suitable granular size through a 12-mesh sieve. The regulated granules are dried at 60° C. for 1 hour. After the sucrose fatty acid ester is added to and mixed with the dried granules, the mixture is wrapped up in an amount of 1.5 g.

Preparation Example 6: Containing a Combination of a Mixture Obtained by the Lactic Fermentation and Ripening of Rice Bran with Lactose

| Prescription | |
|---|---|
| Product obtained by the lactic fermentation and ripening of rice bran | 600 ml |
| Lactose | 473 g |
| Esculent pigment Yellow No. 4 | 25 mg |
| Esculent pigment Yellow No. 5 | 25 mg |
| Refined water | 180 ml |
| Total: | 500 g calculated as solid |

According to the above prescription, a liquid obtained by the dissolution of the components is powderized at an air feed temperature of 155° C. and an air discharge temperature of 55° C. into Toch (Tradename of Fermentative ricebran) powders with the use of a spray dryer.

Preparation Example 7: Containing Pullulan

| | |
|---|---|
| Phytic acid (50%) | 5 g |
| Pullulan | 497.5 g |
| Esculent pigment Yellow No. 4 | 25 mg |
| Esculent pigment Yellow No. 5 | 25 mg |
| Refined water | 800 ml |
| Total: | 500 g calculated as solid |

According to the above prescription, a liquid obtained by the dissolution of the components is powderized at an air feed temperature of 155° C. and an air discharge temperature of 55° C. with the use of a spray dryer.

Preparation Example 8: Containing Chitosan

| Prescription | |
|---|---|
| Liquid phytate composition | 1095 ml |
| Crystalline cellulose | 518.0 g |
| Corn starch | 518.0 g |
| Lactose | Suitable Amount |
| Chitosan | 477.0 g |
| Total: | 3000 g calculated as solid |

According to the above prescription, the component are mixed and kneaded together with the addition of a suitable amount of refined water, and the resulting kneaded product is granulated with a basket of 1.0 mm$\phi$. The resulting granules are regulated to a suitable granular size through a 12-mesh sieve, and is thereafter dried at 60° C. for 1 hour.

Preparation Example 9: Containing Light Silicic Anhydride

| Prescription | |
|---|---|
| Liquid phytate composition | 3285 ml |
| Light silicic anhydride | 1500 g |
| Lactose | Suitable Amount |
| Total: | 3000 g calculated as solid |

According to the above prescription, the component are weighed, mixed, stirred and granulated. The resulting granular product is regulated to a suitable granular size through a 32-mesh sieve, and is then dried at 60° C. for 1 hour into fine granules.

Stability Testing

The preparations according to Preparation Examples 1 to 9 were subjected to stability testing by measuring the amount of residual phytic acid. The results are set forth in Table 2.

TABLE 2

Amounts of Residual Phytic Acid in the Stability Testing of the Preparations According to the Preparation Examples 1-9 (% with respect to the specified contents)

| Samples | Storage Vessels | At the beginning of Storage | After 3 weeks at 60° C. |
|---|---|---|---|
| P.Ex. 1 | Glass Bottle | 98.7 | 100.6 |
| P.Ex. 2 | Glass Bottle | 102.5 | 97.4 |
| P.Ex. 3 | Aluminium Wrapper | 100.4 | 99.1 |
| P.Ex. 4 | Aluminium Wrapper | 98.3 | 100.9 |
| P.Ex. 5 | Aluminium Wrapper | 99.0 | 103.2 |
| P.Ex. 6 | Aluminium Wrapper | 101.7 | 97.6 |
| P.Ex. 7 | Glass Bottle | 104.5 | 102.3 |
| P.Ex. 8 | Glass Bottle | 106.4 | 103.9 |
| P.Ex. 9 | Glass Bottle | 95.7 | 96.9 |
| R.Ex. 1 | Glass Bottle | 97.9 | 69.6 |
| R.Ex. 2 | Glass Bottle | 97.53 | 68.7 |
| R.Ex. 3 | Glass Bottle | 100.5 | 62.0 |

P. Ex. = Preparation Example
R. Ex. = Reference Example

For testing, 22% and 44% aqueous solutions of phytic acid were used in Reference Examples 1 and 2, while pure phytic acid was employed in Reference Example 3.

From the above results, it is appreciated that the examples according to the present invention are much superior to the reference ones in the effects upon the prevention of decomposition and polymerization as well as economical stability of phytic acid.

What is claimed is:

1. A phytic acid composition comprising phytic acid, or a salt thereof, and a powdery, odorless, pale-yellow, water soluble and alcohol soluble substance obtained by treating rice bran with a pectinase, aerobically culturing the thus treated rice bran with a lactobacillus at 35° C. and at a pH of 9.2 to 9.5 for several days, and permitting the culture to stand for about one month, and recovering the product therefrom.

* * * * *